(12) United States Patent
Aalders et al.

(10) Patent No.: US 10,143,786 B2
(45) Date of Patent: *Dec. 4, 2018

(54) BREAST PUMP SYSTEM

(71) Applicant: KONINKLIJKE PHILIPS N.V., Eindhoven (NL)

(72) Inventors: Arnold Aalders, Eindhoven (NL); Hassan El Barakat, Eindhoven (NL); Theodorus Johannes Adrianus Maria Den Bekker, Eindhoven (NL); Cornelis Johannes Janson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/663,993

(22) Filed: Jul. 31, 2017

(65) Prior Publication Data

US 2017/0326279 A1 Nov. 16, 2017

Related U.S. Application Data

(63) Continuation of application No. 14/422,026, filed as application No. PCT/EP2013/063402 on Jun. 26, 2013, now Pat. No. 9,724,453.

(Continued)

(30) Foreign Application Priority Data

Sep. 7, 2012 (EP) ..................... 12183514

(51) Int. Cl.
*A61M 1/06* (2006.01)
*A61M 1/00* (2006.01)
*F04B 17/04* (2006.01)

(Continued)

(52) U.S. Cl.
CPC ............ *A61M 1/06* (2013.01); *A61M 1/0035* (2014.02); *A61M 1/0037* (2013.01);
(Continued)

(58) Field of Classification Search
CPC ........ F04B 49/06; F04B 49/065; F04B 49/10; F04B 2201/0601; F04B 2201/06011;
(Continued)

(56) References Cited

U.S. PATENT DOCUMENTS 5,795,328 A 8/1998 Barnitz
6,673,036 B1 1/2004 Britto
(Continued)

FOREIGN PATENT DOCUMENTS

DE 3820211 A1 11/1988
JP 2011141019 A 7/2011

OTHER PUBLICATIONS

Karan Prakash, Tiagoroth, Karensoh, A mad writer and 2 others: How to Measure Inductance:, Jun. 24, 2012, XP002712413, Retrieved from the Internet: URL:http://www.wikihow.com/Measure-Inductance (retrieved on Sep. 3, 2013 Measuring Inductance Using a Resistor: Connect the inductor coil in series with a resistor . . . : p. 3.

*Primary Examiner* — Bryan Lettman

(57) ABSTRACT

A breast pump system includes a solenoid valve and a power source. The power source is arranged to supply electrical power to the solenoid valve so as enable the solenoid valve to move between first and second positions. The breast pump system also includes a controller configured to detect a change in inductance of the solenoid valve that is indicative of the solenoid valve moving from first to second position and a control action in which the vacuum pump is stopped.

16 Claims, 8 Drawing Sheets

Related U.S. Application Data

(60) Provisional application No. 61/697,850, filed on Sep. 7, 2012.

(51) Int. Cl.
    *F04B 49/06*     (2006.01)
    *F04B 49/10*     (2006.01)

(52) U.S. Cl.
    CPC .......... *F04B 17/042* (2013.01); *F04B 49/06* (2013.01); *F04B 49/10* (2013.01); *F04B 2201/06* (2013.01); *F04B 2203/0402* (2013.01)

(58) Field of Classification Search
    CPC ........ F04B 2201/06012; F04B 2201/06; F04B 49/22; F16K 31/0675; A61M 1/06; A61M 1/0037; A61M 1/0035
    See application file for complete search history.

(56) References Cited

U.S. PATENT DOCUMENTS

| | | | |
|---|---|---|---|
| 7,432,721 B2 * | 10/2008 | Rober | H01F 7/1844 137/1 |
| 7,569,031 B2 * | 8/2009 | Britto | A61M 1/06 604/315 |
| 7,782,590 B2 * | 8/2010 | Bedingfield | H01F 7/1805 361/144 |
| 8,109,901 B2 | 2/2012 | Bryan | |
| 2005/0043677 A1 | 2/2005 | Kelly | |
| 2009/0001302 A1 * | 1/2009 | Murayama | F16K 31/0675 251/65 |
| 2010/0121266 A1 | 5/2010 | Bryan | |

* cited by examiner

BREAST PUMP SYSTEM

CROSS-REFERENCE TO RELATED APPLICATION

The present application is a continuation of co-pending U.S. patent application Ser. No. 14/422,026, filed Feb. 17, 2015, which is the U.S. National Phase application under 35 U.S.C. § 371 of International Application No. PCT/EP2013/063402, filed on Jun. 26, 2013, which claims the benefit of U.S. Provisional Application No. 61/697,850 filed on Sep. 7, 2012 and International Application 12183514.4 filed on Sep. 7, 2012. These applications are hereby incorporated by reference herein.

FIELD OF THE INVENTION

The present invention relates to a breast pump system.

BACKGROUND OF THE INVENTION

A breast pump system comprises a breast pump acting as an expression unit, and an operating unit to operate the breast pump. The expression unit has a funnel which receives the breast and a receptacle in which the expressed milk is collected. The operating unit comprises a vacuum pump driven by a motor. In use, the vacuum pump applies a vacuum to the breast which enables milk to be expressed. The vacuum is applied to the breast either directly or via a membrane located in the expression unit which deforms and so causes a vacuum to be generated in the funnel.

It is known to provide a breast pump system in which a cyclical pressure differential vacuum is applied to the breast. This is achieved by the vacuum pump generating a vacuum exerted on the breast. Thereafter, the pressure from the vacuum is released by the use of a solenoid valve which temporarily opens. After the vacuum has been released, the solenoid valve closes so that the vacuum pump can build up a vacuum again. The opening and closing of the solenoid valve is repeated such that the breast pump system uses a cyclic pressure profile in order to express milk from the breast.

The solenoid valve of the breast pump system is configured to be closed when a vacuum is applied to the breast. However, if the solenoid valve fails to open so as to release the vacuum, the pumping of the vacuum pump will continue to build up the vacuum pressure to a maximum vacuum pressure allowed by the breast pump system. This maximum vacuum pressure is normally limited by an over-vacuum valve.

DE 3820211 A1 discloses a method and device for limiting the reduced pressure of an aspirator working with an aspiration phase and a venting phase.

U.S. Pat. No. 5,795,328 A discloses a vacuum system and a method of operating a vacuum system. The system comprises a vacuum line, a pump, a pump motor, a pressure adjusting assembly, a pressure sensor and a control means. The pump is connected to the vacuum line for drawing fluids therefrom, and the motor is connected to the pump to drive the pump. The pressure adjusting assembly is connected to the vacuum line for conducting fluid into that line at an adjustable rate. The pressure sensor is connected to the vacuum line to generate a pressure signal representing the pressure in the vacuum line. The control means receives the pressure signal and generates a system control signal that is used to adjust the pressure in the vacuum line.

SUMMARY OF THE INVENTION

It is an object of the invention to provide a breast pump system which substantially alleviates or overcomes the problems mentioned above.

According to the present invention, there is provided a breast pump system comprising a solenoid valve, a power source arranged to supply electrical power to the solenoid valve so as to enable the solenoid valve to move between a first and a second position, and a controller configured to detect a change in inductance of the solenoid valve which is indicative of the solenoid valve moving from the first to the second position and a resistor that is connected in series with the solenoid valve and the power source, wherein the controller is arranged to detect a voltage across the resistor, when the resistor is connected to a reference voltage or to ground, or to detect a voltage at a node between the solenoid valve and the resistor, when the resistor is connected to ground.

This provides the advantage that the location of the solenoid can be determined. For example, the change in inductance may be indicative of the solenoid valve being in an opened position so as to release the vacuum. Thus, detecting the change in inductance may be used as an input for a safety measure for breast pump systems.

Further, this provides the advantage that a deviation from a normal current profile can be detected.

In one embodiment, the controller may be configured to detect the change in inductance by detecting a deviation from a normal current profile flowing through the solenoid valve.

An advantage of this arrangement is that the change in inductance can easily be detected.

Preferably, the solenoid valve may comprise a first and a second terminal, the first terminal being connected to the power source and the second terminal being connected to the resistor.

The breast pump system may further comprise an amplifier connected to the resistor, wherein the amplifier is arranged to amplify the voltage detected across the resistor.

This provides the advantage that the resistor connected to the solenoid valve can be a very low resistor so as to only provide a small detectable voltage. The small detectable voltage can then be amplified using the amplifier.

In one embodiment, the breast pump system may comprise a pulse-width modulation controller arranged to switch the current through the solenoid valve according to a pulse-width modulation control scheme, and the amplifier is configured to further act as a low pass filter.

This provides the advantage that the pulse-width modulation controller controls the voltage across the solenoid valve and the low pass filter allows low frequencies to pass through but filters out high frequencies generated by the pulse-width modulation controller so as to generate a more stable voltage and to remove noise.

Preferably, the controller may comprise an analogue-to-digital converter to measure the voltage detected across the resistor.

This provides the advantage that the voltage detected can be measured and so compared to other voltage readings. Thus, measuring the change in inductance may be used as an input for a safety measure for breast pump systems.

In an alternative embodiment, the electrical power supplied to the solenoid valve may be reduced when the change in inductance has been detected.

This provides the advantage that when the change in inductance is indicative of the solenoid valve moving from a first to a second position so as to open an air passage in order to reduce the vacuum in the expression unit, less energy is required to operate the breast pump system. It also is more energy efficient.

Preferably, the breast pump system may further comprise a vacuum pump configured to be controlled by the controller, wherein the controller is arranged to switch off the vacuum pump when the controller does not detect a change in inductance of the solenoid valve.

This provides the advantage that in the embodiment wherein a change in inductance is indicative of the solenoid valve moving from a first to a second position so as to open an air passage, the controller can be configured to switch off the vacuum pump when the controller does not detect a change in inductance of the solenoid valve so that the vacuum generated by the vacuum pump will not continue to increase. This configuration thereby stops the vacuum pump from building up a vacuum in contrast to breast pump systems which use an over-vacuum valve to prevent the vacuum to extend beyond a safety limit. The breast pump systems using an over-vacuum valve continue building up vacuum until the safety limit of the system has been reached. The safety limit is usually a vacuum level uncomfortable to the user.

The controller may compare the voltage detected at the node with a pre-determined value, and if the voltage is lower than said pre-determined value, the controller may determine that the solenoid valve is opened.

In another embodiment, the controller may detect a voltage at the node within a pre-determined time window and may compare the voltage detected with a predetermined value, and if the voltage is lower than said pre-determined value, the controller may determine that the solenoid valve is opened.

In yet another embodiment, the solenoid valve may comprise a housing having a plurality of ports and a pin located in the housing, the pin being movable within the housing when the solenoid valve moves between its first and second positions in response to the power source supplying electrical power to the solenoid valve such that the pin redirects the airflow to one or more ports.

Preferably, the solenoid valve may be a four-port two-position valve.

This provides the advantage that a very compliant membrane can be used in the expression unit. Furthermore, the vacuum pump used can be smaller such that the overall size of the breast pump system is reduced, and the vacuum pump uses less energy. Furthermore, the vacuum pump can be configured to run continuously for expression of milk. In another embodiment, the breast pump system may further comprise an expression unit and a vacuum pump, wherein the first position of the solenoid valve enables the vacuum pump to reduce the pressure in the expression unit, and the second position of the solenoid valve enables the vacuum pump to increase the pressure in the expression unit.

Preferably, the solenoid valve may be a first solenoid valve and the breast pump system may comprise a second solenoid valve having a housing formed with a plurality of ports and a pin located in the housing, the pin being moveable within the housing when the second solenoid valve moves between first and second positions so that the pin redirects the airflow to one or more ports.

Preferably, each of the first and the second solenoid valves may be a three-port two-position valve.

This provides the advantage that a very compliant membrane can be used in the expression unit. Furthermore, the vacuum pump used can be smaller such that the overall size of the breast pump system is reduced, and the vacuum pump uses less energy. Furthermore, the vacuum pump can be configured to run continuously for expression of milk.

The breast pump system may further comprise an expression unit and a vacuum pump, wherein the first and second solenoid valves are in their first position, the vacuum pump is enabled to decrease the pressure in expression unit, and when the first and second solenoid valves are in their second position the vacuum pump is enabled to increase the pressure in the expression unit.

According to another aspect of the invention, there is provided a breast pump system comprising a power source and a solenoid valve with a housing having a plurality of ports and a pin movably located in the housing, the solenoid valve being configured to move between first and second positions in response to the power source supplying electrical power to the solenoid valve, and the pin being configured to move in response to the movement of the solenoid valve so that the pin redirects the airflow to one or more ports.

The breast pump system may comprise an expression unit and an operating unit.

In one embodiment, the breast pump system further comprises any of the features claimed in claims 11 to 15.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
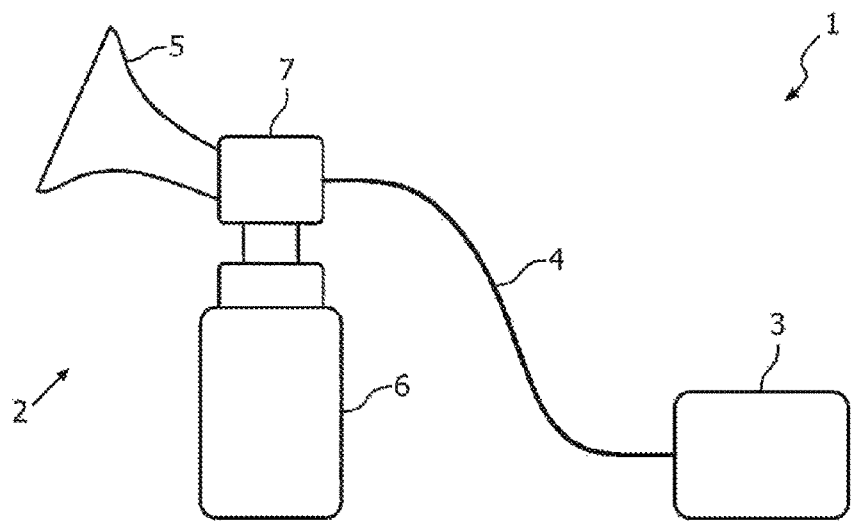
FIG. 1 shows schematic illustration of a breast pump system according to an embodiment of the present invention.

Referring now to the drawings, a breast pump system according to an embodiment is shown in FIG. 1. The breast pump system 1 comprises an expression unit 2 and an operating unit 3 which are connected via a tube 4. However, it shall be understood that the present invention is not limited to such an arrangement. In an alternative embodiment, the operating unit 3 is directly mounted and connected to the main body 7.

The expression unit 2 is formed with a main body 7, a funnel 5 for receiving a breast of a user and a receptacle 6 for collecting the expressed milk. The funnel 5 and the receptacle 6 are connected to the main body 7. The main body comprises a vacuum chamber (not shown). A flexible membrane or diaphragm (not shown) is located in the vacuum chamber. The membrane prevents expressed milk from flowing into the tube 4 leading to the operating unit 3, or in the case where the operating unit 3 is directly mounted and connected to the main body 7, the membrane prevents expressed milk from flowing directly into the operating unit 3.

Figure 2:
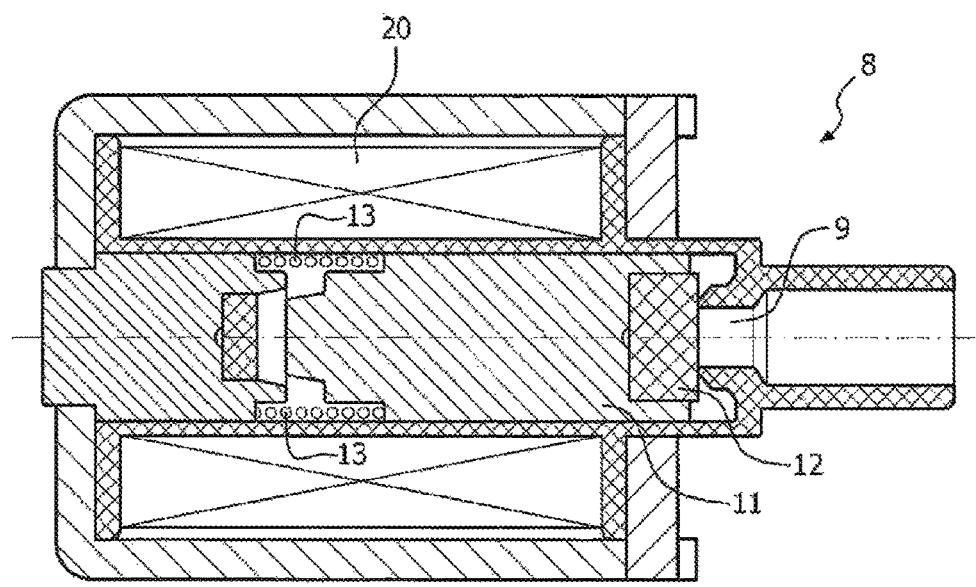
FIG. 2 shows a solenoid valve of the breast pump shown in FIG. 1.
Figure 3:
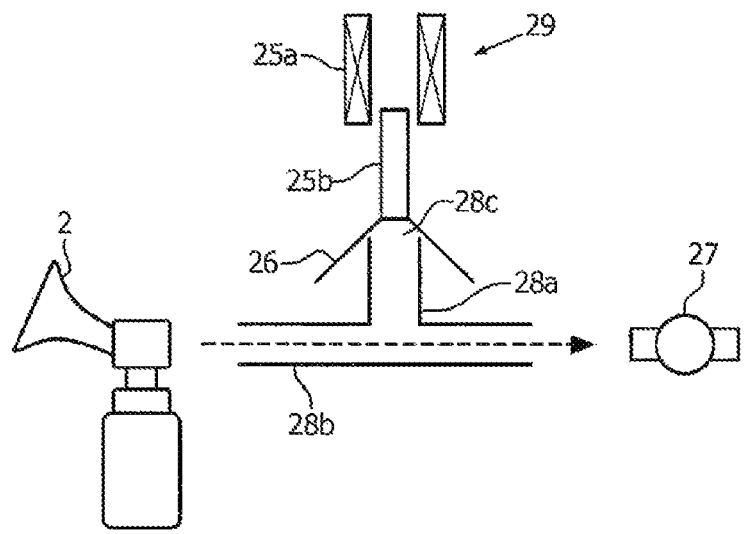
FIG. 3 shows a schematic illustration of a solenoid valve according to another embodiment.
Figure 4:
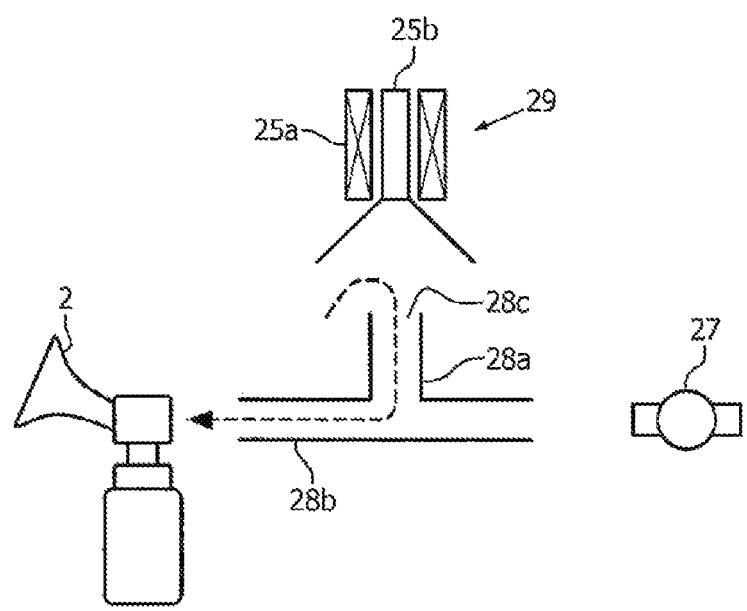
FIG. 4 shows a schematic illustration of the solenoid shown in FIG. 3.

The operating unit 3 comprises a controller 24, a power source 14, a motor (not shown) and a vacuum pump 27. The controller controls the operation of the power source 24, motor and vacuum pump 27. The operating unit 3 further comprises a solenoid valve 8, 29. Embodiments of the solenoid valve are shown in FIGS. 2, 3 and 4.

In use, the vacuum pump 27 applies a vacuum to the membrane located in the connection member 7 so that it deforms. The flexible membrane deforms to create a vacuum in the funnel 5 which in turns applies a vacuum to the breast which enables milk to be expressed. In one embodiment, the membrane inverts as the membrane deforms. However in an alternative embodiment the membrane does not invert.

Although the breast pump system 1 is described as comprising a membrane such that the vacuum is applied indirectly to the breast, it should be understood that in an alternative embodiment, the vacuum is applied directly to the breast of a user. In this embodiment, the breast pump system does not comprise a membrane and the vacuum created by the vacuum pump is applied directly to the breast.

The vacuum is applied to the breast at intervals. That is, a pressure differential is applied on a cyclic basis. After a vacuum has been established, the pressure from the vacuum is released by the use of a solenoid valve 8 which is temporarily being opened. The solenoid valve 8, 29 is an electromechanically operated valve configured to open and close an air passage 9 that connects to the vacuum side of the vacuum pump to ambient air such that when the solenoid valve 8, 29 is in a first position, i.e. closed, the vacuum pump generates a vacuum in the expression unit which enables milk to be expressed from the breast of a user. When the solenoid valve 8, 29 is in a second position, i.e. opened, the vacuum generated by the vacuum pump 27 is released as ambient air flows towards the vacuum or negative pressure created by the vacuum pump such that the pressure exerted on the breast of a user is partially or completely reduced.

An embodiment of the solenoid valve 8 will now be described in detail with reference to FIG. 2. The solenoid valve 8 comprises a magnetic member, for example in the shape of a pin 11. The magnetic member, or pin, is formed from a magnetic material having a north and a south pole. The solenoid valve 8 further comprises a metal coil 20 located about the pin 11. The solenoid valve 8 is controlled by an electrical current flowing through the coil 20. When an electrical current is passed through the coil 20 in a first direction an electromagnetic field is emitted having temporary north and south poles. The north pole of the magnetic pin 11 is attracted to the south pole of the electromagnetic field emitted from the coil 20, and the south pole of the magnetic pin 11 is attracted to the north pole of the electromagnetic field emitted from the coil 20. Thus, due to the attraction of the magnetic pin 11 and the electromagnetic field emitted from the coil 20, the magnetic pin moves relative to said coil 20. In the embodiment shown in FIG. 2, the solenoid valve 8 further comprises a spring 13 located about the pin 11 which urges the pin 11 towards a first position which is against the air passage 9 connecting the vacuum side to ambient air such that the air passage 9 is closed. Thus, a pneumatic seal is formed between the pin 11 and the air passage 9 and air is prevented from flowing through the air passage 9. Furthermore, when the air passage 9 is closed the vacuum pump generates a vacuum in the funnel 5 of the expression unit such that a pressure is exerted on the breast thereby enabling milk to be expressed. When the controller operates the power source such that a current is passed through the coil 20 of the solenoid valve 8, the pin moves through the coil 20 and away from the air passage 9 towards a second position such that the air passage 9 is being opened. When the air passage 9 is opened air flows from the ambient air through the air passage 9 to balance out the negative pressure or vacuum created by the vacuum pump in the funnel 5 of the expression unit 2.

An alternative embodiment of a solenoid valve is schematically illustrated in FIGS. 3 and 4. Although not shown in FIGS. 3 and 4, the expression unit 2 is connected to an air duct 28b in the operating unit 3, and a vacuum pump 27 is connected on the other side of the air duct 28b. An air passage 28a branches off the air duct 28b connecting the expression unit 2 and the vacuum pump 27. The solenoid valve 29 is located at an opened end 28c of the air passage 28a that is connected to ambient air. The solenoid valve 29 comprises a magnetic member which is a hollow pin 25b formed from a magnetic material. The solenoid valve 29 further comprises a metal coil 25a located about the pin 25b. The solenoid valve 29 is operated and functions similarly to the solenoid valve 8 described with reference to FIG. 2 and so a detailed description will be omitted. However, in the embodiment shown in FIGS. 3 and 4 the hollow pin 25b may comprise an element (not shown), however this is optional. Where the hollow pin 25b comprises an element, the element may be fixedly attached to the hollow pin 25b. The element is integrally formed or attached to a flexible membrane 26. In FIGS. 3 and 4, the membrane 26 is illustrated to be located against the opened end 28c of the air passage 28a, however it should be understood that the membrane 26 can extend through and be attached to any part of the operating unit 3 so as to divide the operating unit into different pressurised sections.

The pin 25b is biased towards the opened end 28c of the air passage 28a by the membrane 26 urging the pin 25b towards the end 28c of the air passage 28a. Thus, the membrane 26 acts as a spring. When the pin 25b is biased against the end 28c of the air passage 28, it is in its first position. During the first position, the membrane 26 engages the air passage 28 such that it creates a pneumatic seal and prevents air from flowing through the end 28c of the passage 28a.

Operation of the solenoid valve 29 will now be described with reference to the schematic drawings in FIGS. 3 and 4. FIG. 3 illustrates the pin 25b in its first position. When the pin 25b is in its first position and the vacuum pump 27 pumps air in a direction from the expression unit 2 such that a vacuum is generated in the expression unit 2 as there is no other air inlet or outlet. To release the vacuum in the expression unit 2, the controller operates the solenoid valve 29 such that an electromagnetic field is generated which has sufficient force to urge the pin 25b against the force of the membrane 26 and the vacuum generated in the expression unit 2, towards its second position as seen in FIG. 4. When the pin 25b is in its second position the end 28c of the passage 28a is opened such that air from the ambient air flows through the passage 28a towards the vacuum or negative pressure in the expression unit 2 such that the vacuum is partially or completely reduced.

It shall be understood that the solenoid valve 29 is not limited to the arrangement shown in FIGS. 3 and 4. The solenoid valve 29 can be located elsewhere in an operating unit.

The present invention is not limited to the solenoid valves 8, 29 described above and so any reference to a solenoid valve in the description below is to be understood as including any solenoid valve comprising a coil which produces a magnetic field when current flows therethrough and a magnetic member that moves in response to the emitted electromagnetic field.

When the controller operates the power source so as to open the solenoid valves 8, 29 an electrical current is passed through the coil 20, 25a as previously described. Since the coil 20, 25a has an inductance, the current will rise with some delay and so the force of the electromagnetic field generated by the solenoid valve 8, 29 will also rise with some delay. As soon as the force of the electromagnetic field is high enough the pin 11, 25b will start to move away from the relevant air passage 9 or the end 28c of the air passage 28a so as to open said air passage 9, 28a. The movement of the pin 11, 25b through the coil 20, 25a changes the inductance of the solenoid valve 8, 29, and so the change in inductance is indicative of that the pin 11, 25b has moved from the first position to the second, more specifically that the air passage 9, 28a has been opened.

By measuring the change in inductance of the solenoid valve 8, 29 it can be determined or indicated when the pin 11, 25b has moved from the first to the second position such that the air passage 9, 28a has been opened. The advantage of determining that the air passage 9, 28a has been opened, is that the controller 24 can then continue to operate the vacuum pump 27 and do so safely without exceeding a safety limit. If it cannot be determined that the pin 11, 25b has moved such that the air passage 9, 28a has been opened, or the controller determines that the pin has remained in its first position closing the air passage 9, 28a, the controller will terminate operation of the vacuum pump 27 so as to avoid the pressure to exceed the safety limit.

According to an embodiment of the present invention, the controller is configured to detect a change in inductance of the solenoid valve 8 which is indicative of the pin 11, 25b moving from its first to its second position so as to open the air passage 9, 28a.

In one embodiment of the present invention, the controller 24 is configured to detect the change in inductance by detecting a change in current flowing through the solenoid valve. A change in current is to be understood as a deviation from a normal current profile. A normal current profile for a current, I(t), when the pin 11 is located in its second position is expressed as:

$$I = I_0 \times \left(1 - e^{\frac{-t}{\tau}}\right)$$

Wherein I represents current detected, $I_0$ represents the steady-state current running through the coil dependent on applied voltage and coil characteristics, e represents exponential function, t represents time and τ represents a constant based on the characteristics of the coil. This function represents an exponential increase in voltage.

In an alternative embodiment, the normal current profile for a current is expressed as follows;

$$I = I_0 \times e^{\frac{-t}{\tau}}$$

Wherein I represents current detected, $I_0$ represents the steady-state current running through the coil dependent on applied voltage and coil characteristics, e represents exponential function, t represents time and τ represents a constant based on the characteristics of the coil. This function represents an exponential decrease in voltage.

A normal current profile shall be understood as the expected increase or decrease in current flowing through the solenoid valve 8, 29 relative to the actual supply of current to the solenoid valve 8, 29. A change or a deviation from the normal current profile may be a sudden increase or decrease such as a dip or a bump in the detected current as the current is increased as illustrated by the dotted lines in the schematic illustration in FIG. 5. Alternatively, a change or deviation from the normal current profile may be a sudden increase or decrease such as a dip or a bump in the detected current as the current is decreased as illustrated by the dotted lines in the schematic illustration in FIG. 6.

Figure 7:
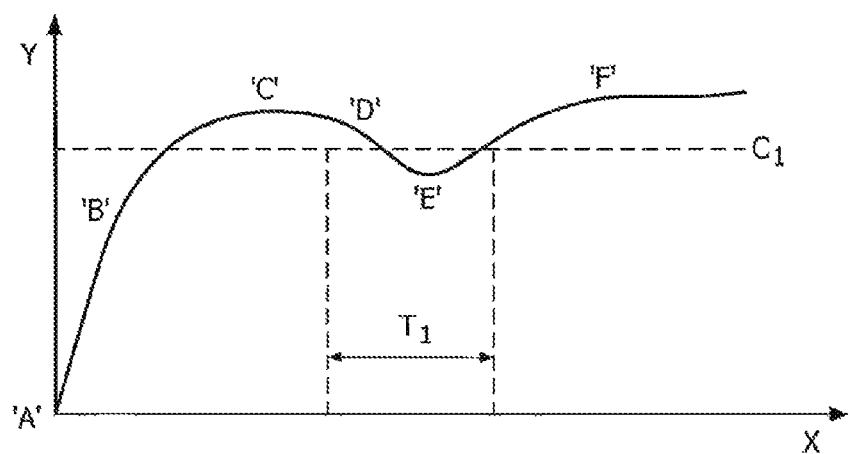
FIG. 7 shows a schematic graph of the level of current (y-axis) flowing through the solenoid valve with time (x-axis)

A schematic graph of current flowing through the solenoid valve 8, 29 according to one embodiment of the present invention is shown in FIG. 7, wherein the y-axis represents current and the x-axis represents time. In this embodiment a deviation from the normal current profile is detected as a sudden decrease or dip in the overall increasing current.

At point 'A' in FIG. 7, the solenoid valve 8, 29 is closed. Electrical current or voltage is then applied to the solenoid valve 8 which causes the current to increase as represented by point 'B'. At point 'C', the current has reached a maximum which shows that the pin 11, 25b is moving to its second position such that the air passage 9, 29 is being opened. As the air passage 9, 28 is being opened, the pin 11, 25b moves through the coil 20, 25a to its second position and this causes the inductance of the solenoid valve 8, 29 to change. This in turn causes the current to decrease as is represented by point 'D'. The current thereafter reaches a dip (point 'E') which represents that the pin has fully moved into its second position. Point 'F' represents the current increasing to a stable level.

Figure 8:
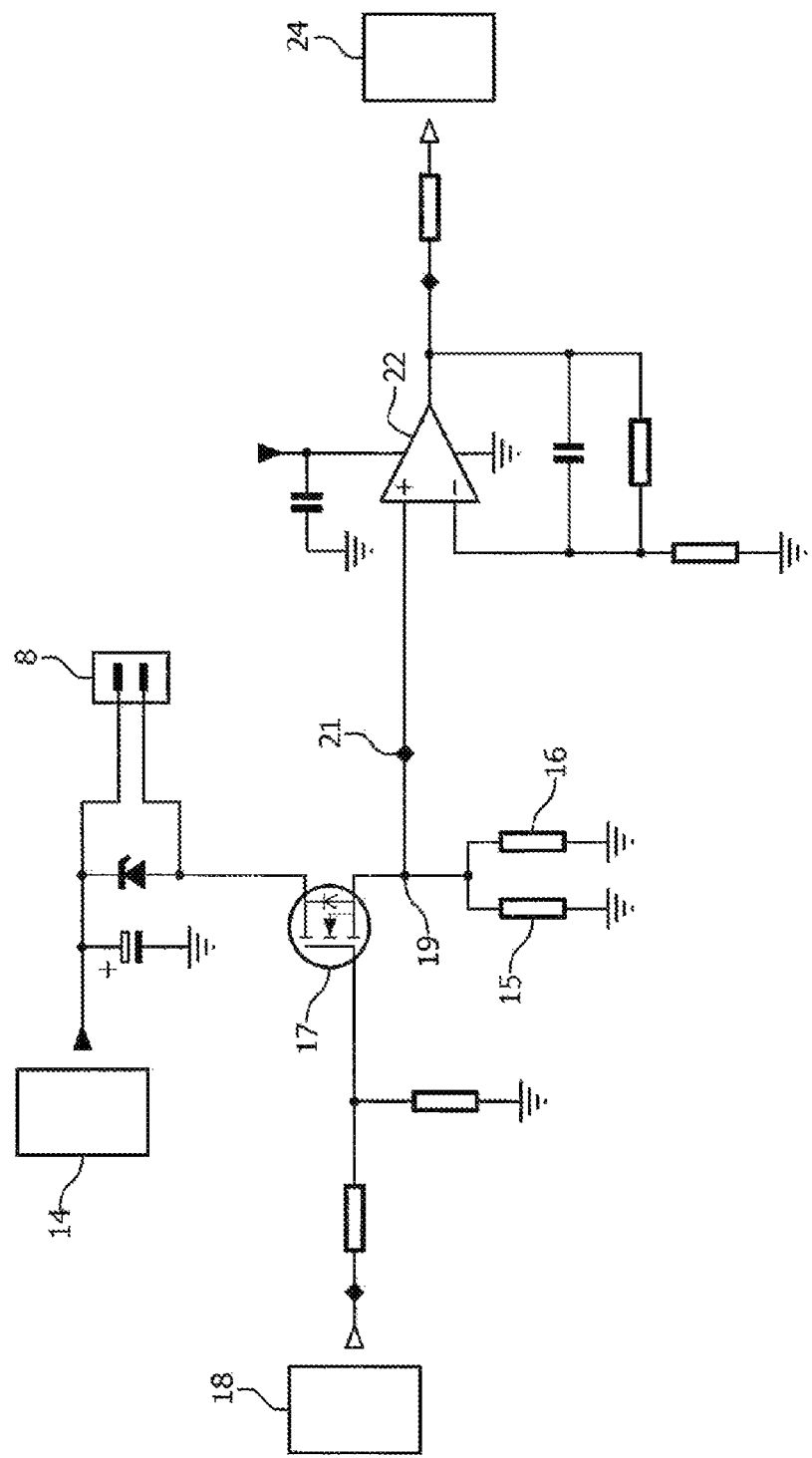
FIG. 8 shows a schematic circuit diagram according to an embodiment of the present invention.

The controller 24 is configured to detect a deviation or change in current flowing through the solenoid valve 8, 29 compared to the normal current profile of the solenoid valve 8, 29 according to an embodiment shown in FIG. 8. FIG. 8 represents an electrical circuit and the components for detecting a deviation or change in current flowing through the solenoid valve 8, 29.

The electrical circuit comprises the power source 14 supplying voltage to the circuit. The solenoid valve 8, 29 comprises a first and a second terminal whereof the first terminal is connected to the power source 14. The second terminal of the solenoid valve 8 is in a preferred embodiment connected to two resistors 15, 16 that are connected to a reference voltage which may be a low voltage, or a voltage lower than 0 Volt, or ground as shown in FIG. 8. However, the two resistors could be replaced by one or more than two resistors. The solenoid valve 8, 29 power source 14 and the resistors 15, 16 are connected in series. Furthermore, the solenoid valve 8 is connected to the two resistors 15, 16 through a field effect transistor (FET) 17. A pulse-width modulation controller 18 is also connected to the FET 17 and is arranged to switch the current through the solenoid valve 8, 29 according to a pulse-width modulation control scheme. The FET 17 ensures that the desired voltage is applied across the solenoid valve 8, 29.

The controller is arranged to detect a voltage 21 across the resistors 15, 16 when the resistors are connected to a reference voltage or to ground. In an alternative embodiment, the controller is arranged to detect a voltage 21 at a node 19 between the solenoid valve 8, 29 and the resistors 15, 16 when the resistors 15, 16 are connected to ground.

An analogue-to-digital converter (ADC) (not shown) is arranged to measure the voltage detected at the node 19 or detected across the resistors 15, 16. The ADC can be part of the electrical circuit shown or it can form part of the controller.

The electrical circuit further comprises an amplifier 22 connected between the ADC and the node 19. The amplifier is arranged to amplify the voltage 21 detected at the node 19 or across the resistors 15, 16 to a level detectable or measurable by the ADC. In one embodiment as shown in FIG. 8, the amplifier functions as a low pass filter. The low pass filter is arranged to have a cut-off frequency lower than a switching frequency of the FET 17. Furthermore, the low pass filter allows low frequencies to pass through but filters out at least high frequencies generated by the pulse-width modulation controller so as to generate a more stable voltage and less noisy voltage. The voltage is then detected by the controller which is represented as number 24 in FIG. 8.

In the embodiment wherein the resistors 15, 16 are connected to a reference voltage, a differential amplifier may be used.

In one embodiment, the controller detects the voltage at the node 19 or across the resistors 15, 16 within a pre-determined time window. The pre-determined time window is configured to extend across the change or deviation in current from the normal current profile. For example, when increasing the current so as to move the pin 11, 25b of the solenoid valve 8, 29 from its first position (closing the air passage 9, 28) to its second position (opening the air passage 9, 28) the pre-determined time window is configured to start after the voltage has peaked (when the inductance changes due to the movement of the pin 11, 25b in the coil 20, 25a) and finish after the expected sudden decrease in voltage (when the pin 11, 25b is fully in its second position). The controller 24 then compares the detected voltage readings with a pre-determined value. If any of the voltage readings is lower than the pre-determined value, the controller 24 determines that the pin 11, 25b has moved to its second position.

Alternatively, the controller 24 determines a difference between the highest voltage reading and the lowest voltage reading, and compares this difference with a predetermined value. If the difference between the highest and lowest voltage readings is higher than a pre-determined value, the controller determines that the pin 11, 25b has moved to its second position.

In yet another alternative embodiment, the controller converts the voltage detected at the node 19 or across the resistors 15, 16 to current and compares either the current detected during the pre-determined time window (see $T_1$ in FIG. 7) and with a predetermined value (see $C_1$ in FIG. 7), or compares the difference of the maximum and minimum current detected with a predetermined value Similarly, if the current detected is lower than the pre-determined value $C_1$ during the pre-determined time window $T_1$, or if the difference between the maximum or minimum current detected is greater than a pre-determined value the controller determines that the pin 11, 25b has moved to its second position in which the air passage 9, 28 is opened.

It shall be appreciated that the invention is not limited to the electrical circuit described with reference to FIG. 8. For example, in an alternative electrical circuit, only a single resistor 15 is used which is connected to the solenoid valve 8, 29 through a FET. Furthermore, in another embodiment the electrical circuit does not comprise a pulse-width modulation controller as a constant voltage is applied to the system and so also a FET is omitted from the electrical circuit. In this embodiment, an electrical switch would be used to switch the power supply to the solenoid valve 8, 29 on or off.

Furthermore, it shall also be appreciated that the above described electrical circuit can be modified such that the current of the motor can be detected by measuring the voltage across the motor.

Advantageously, when the change in inductance has been detected by the controller, the electrical power supplied to the solenoid valve 8, 29 can be reduced. The reason for this is that the pressure from the vacuum dictates the power required to move the pin 11, 25b from its first position in which it closes the air passage 9, 28 to its second position in which it opens the air passage 9, 28. Thus, when the controller 24 has determined that the pin 11, 25b is in its second position the pressure of the vacuum has been released and so therefore less power is required for operating the solenoid valve 8, 29.

When the controller has detected the change in inductance, and compared the voltage or the current or difference in voltage or current with a pre-determined value within a pre-determined time window and determined that the pin 11, 25b has moved to its second position such that the solenoid valve 8, 29 has been opened, the breast pump system functions normally and the controller 24 continues to operate the breast pump system. If the controller 24 does not detect the change in inductance, thus the controller 24 does not detect a decrease or increase in voltage or current within a pre-determined time, the controller 24 is configured to take action. In one embodiment the controller 24 stops the vacuum pump 27 so as to prevent further pressure to be exerted on the breast of the user. This can be achieved by the controller 24 switching off the electric power supplied to the vacuum pump 27. It shall be understood that alternative actions may be taken if the controller 24 does not detect a decrease or an increase in voltage or current. For example, the controller may detect a second voltage reading so as to confirm the status of the solenoid valve 8, 29 before determining whether to continue to operate or stop the vacuum pump 27.

Although the above embodiments refer to a change of inductance when the pin 11, 25b moves from its first position in which the air passage 9 is closed to its second position in which the air passage 9, 28 is opened, it shall be appreciated that the breast pump system may be configured such that when the pin is in its first position it opens an air passage and when the pin is in its second position the pin closes an air passage. In this embodiment, a change in inductance is detected when the pin moves through the coil from its first to its second position such that the change in inductance is indicative of the air passage being closed. Alternatively, the controller can be configured to detect a change in inductance of the solenoid valve which is indicative of the pin moving from a first to a second position, wherein the first and second positions are not associated with opening or closing an air passage but may initiate or stop another mechanical movement or operation or direct air flow in a first and a second direction.

The above description refers to embodiments described with reference to FIGS. 2 to 4, as well as other solenoid valves comprising a coil and a magnetic member which is moveable between a first position and a second position in response to current flowing through the coil. It is to be understood that when the pin of the solenoid is described above as being in its first position, the solenoid valve is also in its first position. Similarly, when the pin is described above as being in its second position the solenoid valve is also in its second position. The first and the second positions of the solenoid valve can either be when the pin has opened or closed an air passage. Alternatively, the first position of the solenoid valve can be when the pin is in its first position to direct air flow in a first direction and the second position can be when the pin is in its second position in which it directs air flow in a second direction. In yet another embodiment, the first position of the solenoid valve can be when the pin is in its first position initiating or stopping a mechanical movement or operation, and the second position of the solenoid valve can be when the pin is in its second position initiating or stopping a mechanical movement or operation.

Furthermore, it shall be understood that the embodiments of the solenoid valve of the present invention are not limited to comprising a pin. The solenoid valve may comprise a magnetic member of various shapes that move relative to a coil when supplied with current. Moreover, the magnetic member may be magnetised by exposing it to an external magnetic field. Due to the magnetic properties of the magnetic member, the magnetic member forms either a temporary or a permanent magnet after the external field has been applied and removed.

According to another embodiment of the present invention which will now be described, the solenoid valve 8, 29 does not close or open an air passage connecting the vacuum side of the vacuum pump with the ambient air instead the solenoid valve has first and second positions, wherein the two positions direct air flow in different directions.

Figure 5:
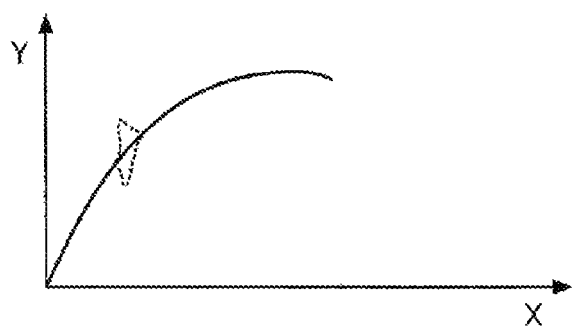
FIG. 5 shows a schematic graph of a normal current profile as the current is increasing wherein the y-axis represents current and the x-axis represents time, and the dotted lines represent changes in the normal current profile.
Figure 6:
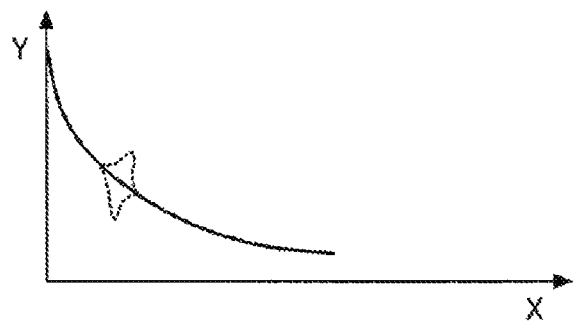
FIG. 6 shows a schematic graph of a normal current profile as the current is decreasing wherein the y-axis represents current and the x-axis represents time, and the dotted lines represent changes in the normal current profile.
Figure 9:
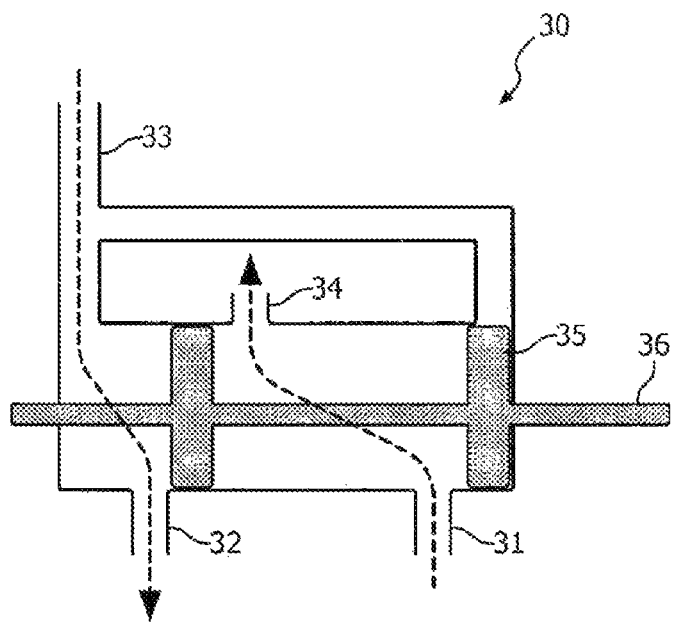
FIG. 9 shows a 4/2 solenoid valve in a first position.
Figure 10:
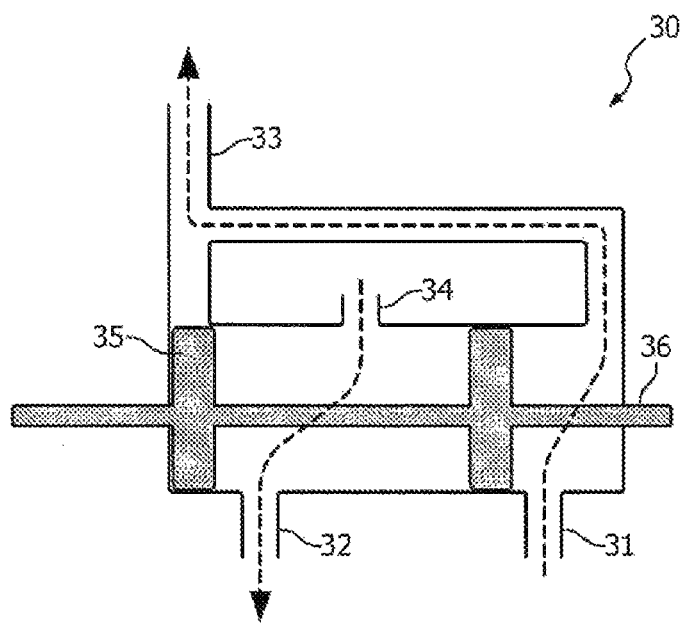
FIG. 10 shows the 4/2 solenoid valve of FIG. 9 in a second position.

One embodiment is illustrated in FIGS. 9 to 12, and in this embodiment the operating unit comprises a four-port two-position (4/2) solenoid valve 30. The solenoid valve comprises a housing having four ports as is best illustrated in FIGS. 5 and 6. The vacuum pump is represented by number 37 in FIGS. 11 and 12. The outlet of the vacuum pump 37 is connected to a first port 31 and the inlet of the vacuum pump 37 is connected to a second port 32. A third port 33 is connected to the expression unit 2 and the fourth port 34 is connected to ambient air as is best seen in FIGS. 9 and 10.

The solenoid valve further comprises a pin 35 similar to the pin of the embodiments described with reference to FIGS. 2 to 4. The pin 35 is located in the housing and it has an end that extends out of the housing and through a coil (not shown). The pin 35 is movable between a first and a second position through the coil when supplied with electrical current as described with reference to FIGS. 2 to 4 above. In an alternative embodiment, a spool is located in the housing and an end of the spool is attached to a pin located in the coil such that when the coil is provided with current the pin moves which in turn causes the spool to move within the housing.

Figure 11:
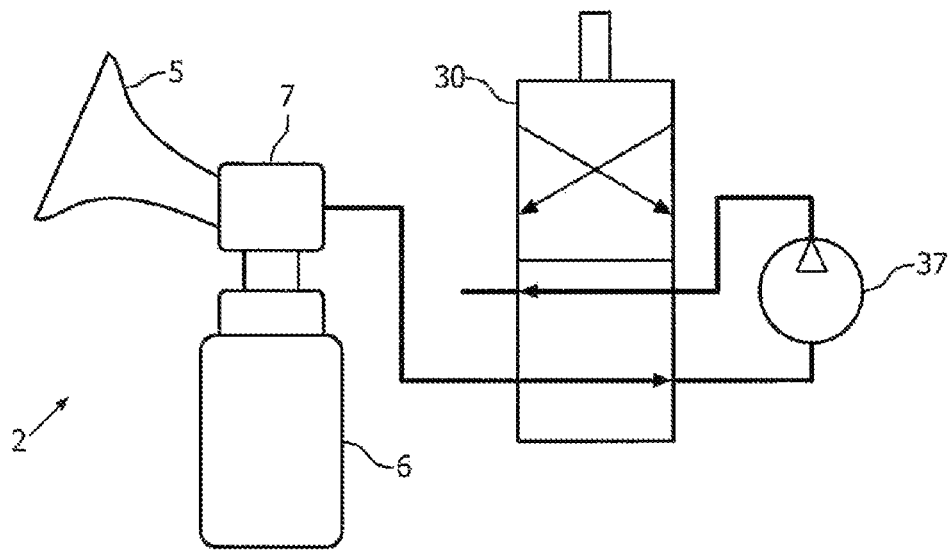
FIG. 11 shows a schematic illustration of the breast pump system comprising a 4/2 solenoid valve, wherein the 4/2 solenoid valve is in its first position as illustrated in FIG. 9.

In FIGS. 9 and 11, the pin 35 is located in its first position and when the vacuum pump 37 is being operated by the controller 24 air is sucked from the expression unit 2 connected to port 33 into the housing of the solenoid valve 30 and out through port 32 connected to the vacuum pump inlet, as is indicated by the arrow in FIG. 9. The vacuum pump pumps the air into the housing through port 31 and the air exits the housing through port 34 connected to ambient air.

Figure 12:
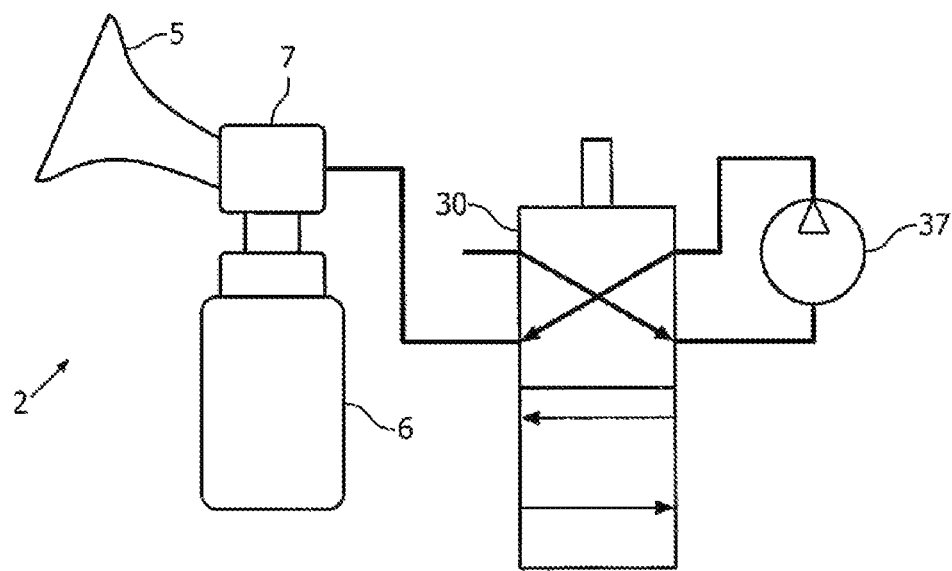
FIG. 12 shows a schematic illustration of the breast pump system comprising a 4/2 solenoid valve, wherein the 4/2 solenoid valve is in its second position as illustrated in FIG. 10.

When the controller operates the solenoid valve 30 such that the pin 35 moves to its second position as shown in FIGS. 10 and 12, the vacuum pump sucks air from the ambient air connected to port 34 and through the housing and out through port 32 connected to the vacuum pump inlet. The air is then pumped into the housing through port 31 connected to the vacuum pump outlet, and the air exits the housing via port 33 connected to the expression unit 2. The arrows in FIGS. 9 and 10 represent the direction of the airflow.

This arrangement enables the vacuum pump 37 to pump in a single direction and to pump continuously throughout the use of the breast pump system. As described above, when the pin 35 is in its first position as shown in FIGS. 9 and 11, the pressure in the expression unit is reduced such that a vacuum is applied to the breast received in the funnel 5 of the expression unit 2. When the pin 35 is moved to its second position as shown in FIGS. 10 and 12, the vacuum pump directs air from the ambient air to the funnel 5 of the expression unit 2 such that the pressure is increased in the expression unit. Thus, the vacuum initially generated by the vacuum pump is reduced partially or completely. The solenoid valve 30, or more specifically the pin 35, continuously moves between its first and second positions such that a cyclic pressure profile is applied to the breast.

According to yet another embodiment of the invention, the breast pump system comprises two solenoid valves that are configured to be in first and second positions so as to direct air flow in different directions.

Figure 13:
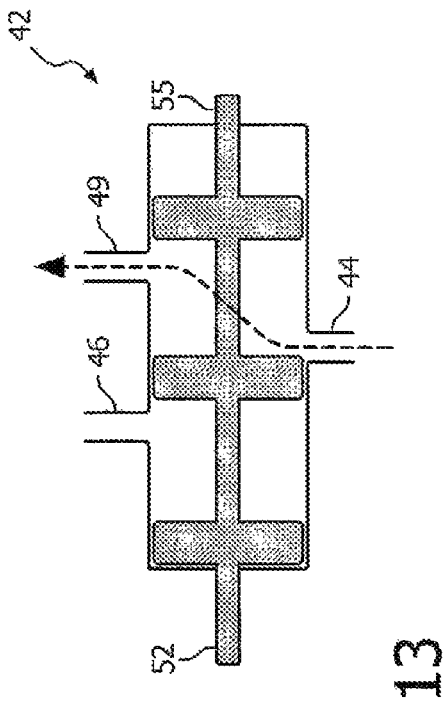
FIG. 13 shows first and second 3/2 solenoid valves in their first position.
Figure 14:
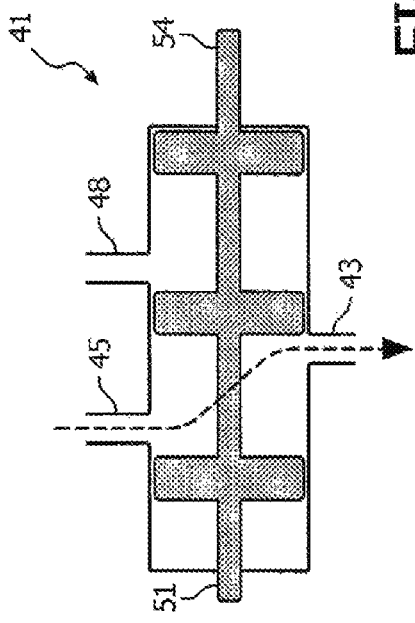
FIG. 14 shows the first and second 3/2 solenoid valves of FIG. 13 in their second position.

One such embodiment is illustrated in FIGS. 13 to 16, and in this embodiment the operating unit comprises first and second solenoids that are three-port two-position (3/2) solenoid valves 41, 42. Each solenoid valve comprises a housing having three ports as is best illustrated in FIGS. 13 and 14. The vacuum pump is represented by number 47 in FIGS. 15 and 16. The outlet of the vacuum pump 47 is connected to a first port 43 of the first solenoid valve 41 and the inlet of the vacuum pump 47 is connected to a first port 44 of the second solenoid valve 42. A second port 45 of the first solenoid valve 41 and a second port 46 of the first solenoid valve 42 are each connected to the expression unit 2. A third port 48 of the first solenoid valve 41 and a third port 49 of the second solenoid valve 42 are each connected to ambient air. This is best seen in FIGS. 13 and 14.

A pin 51, 52 is located in each housing of the solenoid valves 41, 42 and the pins 51, 52 are movable between a first and a second position. Each pin has an end that extends out of the respective housing and through a coil (not shown). Each pin 51, 52 is movable between a first and a second position through respective coil when supplied with electrical current as described with reference to FIGS. 2 to 4 above. In an alternative embodiment, a spool is located in each housing and an end of each spool is attached to a pin located in each coil such that when each coil is provided with current each pin moves which in turn causes each spool to move within respective housing.

Figure 15:
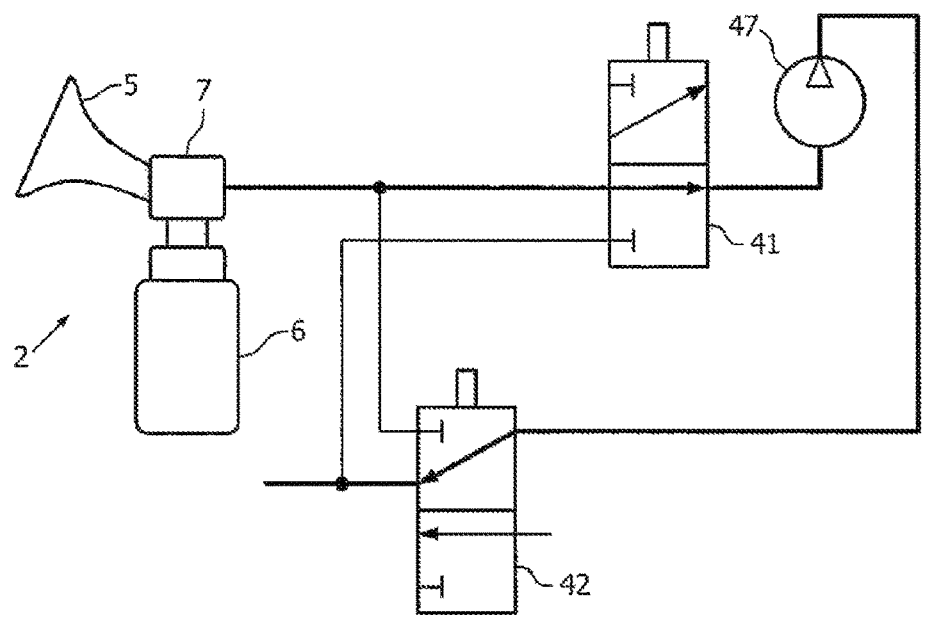
FIG. 15 shows a schematic illustration of the breast pump system comprising two 3/2 solenoid valves, wherein the 3/2 solenoid valves are in their first position as illustrated in FIG. 13.

In FIGS. 12 and 15, the pins 51, 52 of each solenoid valve 41, 42 are located in their first positions and when the vacuum pump 47 is being operated by the controller air is sucked from the expression unit 2 connected to second port 45 of the first solenoid valve 41 into its housing and out through first port 43 connected to the vacuum pump inlet, as is indicated by the arrow in FIG. 13. Then, the vacuum pump pumps the air into the housing through first port 44 of the second solenoid valve 42 and the air exits the housing of the second solenoid valve 42 through third port 49 which is connected to ambient air.

Figure 16:
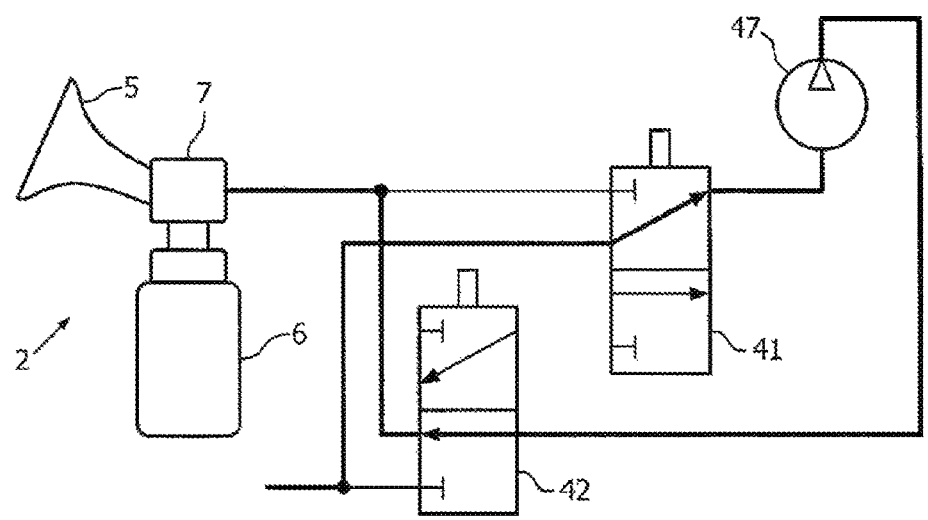
FIG. 16 shows a schematic illustration of the breast pump system comprising two 3/2 solenoid valves, wherein the 3/2 solenoid valves are in their second position as illustrated in FIG. 14.

When the controller operates each solenoid valve 41, 42 such that the pins 51, 52 move to their second positions as shown in FIGS. 14 and 16, the vacuum pump 47 sucks air from the ambient air connected to the third port 48 of the first solenoid valve 41 and through the housing and out through first port 43 of the first solenoid valve 41 connected to the vacuum pump 47 inlet. The air is then pumped into the housing of the second solenoid valve 42 through the first port 44 of the second solenoid valve 42 connected to the vacuum pump outlet, and the air exits the housing via port second port 46 connected to the expression unit. The arrows in FIGS. 13 and 14 represent the direction of the airflow.

The arrangement of the 3/2 solenoid valves 41, 42 enables the vacuum pump to pump in a single direction and to pump continuously throughout the use of the breast pump system. As described above, when the pins 51, 52 are in their first positions as shown in FIGS. 13 and 15, the pressure in the expression unit is reduced such that a vacuum is generated in the funnel 5 of the expression unit 2. When the pins are moved to their second position as shown in FIGS. 14 and 16, the vacuum pump pumps air from the ambient air to the funnel 5 of the expression unit 2 such that the pressure in the expression unit increases. The vacuum in the expression unit is thereby partially or completely reduced. The solenoid valves 41, 42, or more specifically the pins 51, 52, continuously move between their first and second positions such that a cyclic pressure profile is applied to the breast.

Advantageously, a solenoid valve or a plurality of solenoid valves as described above which comprises a housing having a plurality of ports and a pin located therein, enables a smaller pump to be used such that the over all size of the operating unit can be reduced. This arrangement also reduces the amount of energy used and so is cheaper to run. Furthermore, the vacuum pump 37, 47 can be switched on for continuous expression of milk.

The embodiments of the breast pump system having a 4/2 solenoid valve or two 3/2 solenoid valves can be configured such that the controller is arranged to detect a change in inductance of the solenoid valve when the pin moves through the coil. The change in inductance would be indicative of that the solenoid valve(s) has moved from their first to their second position.

Furthermore, it shall be understood that the controller can be configured to detect the change in inductance by detecting a change or deviation in current flowing through the solenoid valve as described above with reference to FIGS. 2 to 4. However, the change detected in the current would indicate that the solenoid valve(s), or more specifically, the pin(s) of the solenoid valve(s) has moved from its first to its second position.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump system comprising:
   a vacuum pump configured to be run, wherein the vacuum pump is adapted to be pneumatically coupled, via a passageway, to an expression unit, the expression unit adapted to be coupled to a breast to obtain milk in response to an applied pressure change;
   a solenoid valve pneumatically coupled to the passageway, said solenoid valve including a magnetic member arranged to move alternately between (i) a first position at which the passageway is pneumatically sealed from ambient air flow, and (ii) a second position at which the passageway is open to ambient air flow;
   a power source arranged to supply electrical power to the solenoid valve; and
   a controller configured to detect a change in an inductance of the solenoid valve that is indicative of the magnetic member moving from the first position to the second position and to control a first operation of at least one of the solenoid valve and the vacuum pump in dependence on detection of said change in the inductance, wherein the controller is adapted to control a second operation of at least one of the solenoid valve and the vacuum pump when the controller does not detect the change in the inductance of the solenoid valve within a predetermined time period that corresponds to a period (i) beginning as the magnetic member is moving to its second position which results in the change in the inductance and (ii) ending subsequent to the magnetic member having fully moved into its second position, but prior to a current in the solenoid valve increasing to a stable level.

2. The breast pump system according to claim 1, wherein the controller is configured to detect the change in the inductance by detecting a deviation of current flowing through the solenoid valve from a predetermined solenoid current profile.

3. The breast pump system according to claim 2, wherein the solenoid valve comprises a first and a second terminal, the first terminal being connected to the power source and the second terminal being connected to a resistor that is electrically connected in series with the solenoid valve.

4. The breast pump system according to claim 3, further comprising an amplifier electrically connected to the resistor, said amplifier being adapted to amplify a voltage detected across the resistor produced by the solenoid current flowing through the resistor.

5. The breast pump system according to claim 4, further comprising a pulse-width modulation controller arranged to switch the current flowing through the solenoid valve according to a pulse-width modulation control scheme.

6. The breast pump system according to claim 4, wherein the controller comprises an analog-to-digital converter to measure the voltage detected across the resistor.

7. The breast pump system according to claim 1, wherein in the first operation the electrical power supplied to the solenoid valve is reduced when the change in inductance has been detected.

8. The breast pump system according to claim 1, wherein the first position of the magnetic member of the solenoid valve enables the vacuum pump to reduce a pressure in the expression unit to a predetermined negative pressure without exceeding a safety limit, wherein the second position of the magnetic member of the solenoid valve enables the vacuum pump to pump ambient air to the expression unit to increase the pressure in the expression unit from the predetermined negative pressure, and wherein the controller is adapted to switch off the vacuum pump when the controller does not detect the change in the inductance of the solenoid valve within the predetermined time period, wherein switching off the vacuum pump stops a further increase in negative pressure in the expression unit beyond the predetermined negative pressure exceeding the safety limit.

9. The breast pump system according to claim 1, wherein the solenoid valve comprises a housing that includes:
   a. a first port pneumatically coupled to an outlet of the vacuum pump;
   b. a second port pneumatically coupled to an inlet of the vacuum pump;
   c. a third port pneumatically coupled to the expression unit, and
   d. a fourth port pneumatically coupled to a source of ambient air;

and where the magnetic member in said solenoid valve is arranged for movement so as to direct airflow through the solenoid valve such that:

when the magnetic member is in the first position, the vacuum pump is operable to produce an air flow from the expression unit into the inlet of the vacuum pump and then from the outlet of the vacuum pump to the source of ambient air, and when the magnetic member is in the second position, the vacuum pump is operable to produce an air flow from the source of ambient air into the inlet of the vacuum pump and then from the outlet of the vacuum pump to the expression unit.

10. The breast pump system according to claim 9, wherein the solenoid valve comprises a four-port two-position valve.

11. The breast pump system according to claim 10, wherein the predetermined solenoid current profile is a normal profile for the current flowing through the solenoid as the magnetic member moves between the first and second positions.

12. The breast pump system according to claim 9, further comprising a second solenoid valve also coupling the expression unit to the vacuum pump, wherein said second solenoid valve comprises a housing formed with a plurality of ports and including a magnetic member arranged for movement between first and second positions so as to redirect an airflow from at least one port to another.

13. The breast pump system according to claim 12, wherein each of the first and the second solenoid valves comprise a three-port two-position valve.

14. The breast pump system according to claim 13, wherein both of the first and the second solenoid valves are operated such that, when their respective magnetic members are in their first position, the vacuum pump is enabled to decrease the pressure in expression unit, and when their respective magnetic members are in their second position the vacuum pump is enabled to increase the pressure in the expression unit.

15. The breast pump system according to claim 1, wherein the passageway has an opening that is pneumatically sealed when the magnetic member is in the first position and is open to ambient air flow when the magnetic member is in the second position.

16. The breast pump system according to claim 15, further comprising a flexible membrane coupled to the magnetic member for performing said alternate sealing and opening of said opening in the passageway.

* * * * *